US006677415B1

(12) United States Patent
O'Connor et al.

(10) Patent No.: US 6,677,415 B1
(45) Date of Patent: Jan. 13, 2004

(54) METHOD OF COMPRESSION MOULDING OF POLYMER POWDER AND PRODUCT PRODUCED

(75) Inventors: John Joseph O'Connor, 9 Beaumont Road, Headington, Oxford (GB), OX3 8JN; Christopher Paul Buckley, Oxford (GB); Junjie Wu, Oxford (GB)

(73) Assignee: John Joseph O'Connor, Oxford (GB)

( * ) Notice: Subject to any disclaimer, the term of this patent is extended or adjusted under 35 U.S.C. 154(b) by 0 days.

(21) Appl. No.: 09/926,291

(22) PCT Filed: Apr. 6, 2000

(86) PCT No.: PCT/GB00/01281

§ 371 (c)(1), (2), (4) Date: Jan. 15, 2002

(87) PCT Pub. No.: WO00/59701

PCT Pub. Date: Oct. 12, 2000

(30) Foreign Application Priority Data

Apr. 6, 1999 (GB) .............................................. 9907843

(51) Int. Cl.[7] .......................... C08F 14/18; A61F 2/30; B29B 11/12
(52) U.S. Cl. ............. 526/250; 264/331.14; 264/331.17; 526/351; 526/352; 623/18.11; 623/23.58
(58) Field of Search .......................... 623/23.58, 18.11; 264/109–128, 331.14, 331.17; 526/250, 351, 352

(56) References Cited

U.S. PATENT DOCUMENTS 5,030,402 A * 7/1991 Zachariades ................ 264/138
5,316,711 A * 5/1994 Throne ........................ 264/68
6,066,280 A * 5/2000 Abbondanza et al. ....... 264/126

FOREIGN PATENT DOCUMENTS

WO WO 97 29895 A 8/1997

OTHER PUBLICATIONS

Wool R.P. et al., "A theory of crack healing in polymers", J. Appl. Phys., vol. 52, No. 10, 1981, pp. 5953–5963, XP000907656.
Wool R.P. et al., "Welding of polymer interfaces", Polym. Eng. Sci., vol. 29, No. 19, 1989.
Kurelec L. et al., "Chain mobility in polymer systems between solid and melt: sintering via the mobile hexagonal phase", Polym. Mater. Sci. Eng., vol. 81, Aug. 1999, pp. 271–272, XP000921498.

* cited by examiner

Primary Examiner—Stephen J. Lechert, Jr.
(74) Attorney, Agent, or Firm—Bacon & Thomas, PLLC

(57) ABSTRACT

A process of compression moulding an article from a polymer powder comprising; a) applying a polymer powder to a mould; b) compacting the polymer powder by the application of a pressure P; c) raising the temperature of the surface of the mould to a value above the melting temperature of the polymer powder; and d) maintaining a temperature $T_M$ at the surface of the mould for a period of time $t_M$ and then cooling to a temperature below the crystallisation temperature of the polymer; where $T_M$ and $t_M$ are controlled so as to provide a moulded article comprising a polymer of predetermined maximum reptated molecular weight. The compression moulded articles produced by this process are useful as orthopaedic prostheses, such as components of knee, hip, shoulder, elbow, wrist, ankle, finger or toe joint replacements.

11 Claims, 7 Drawing Sheets

(a)

(b)

FIG. 1.
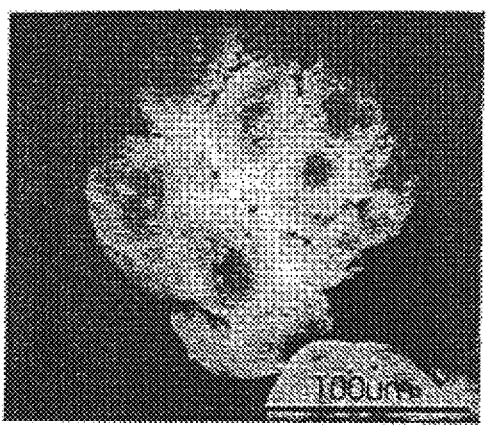
(a)
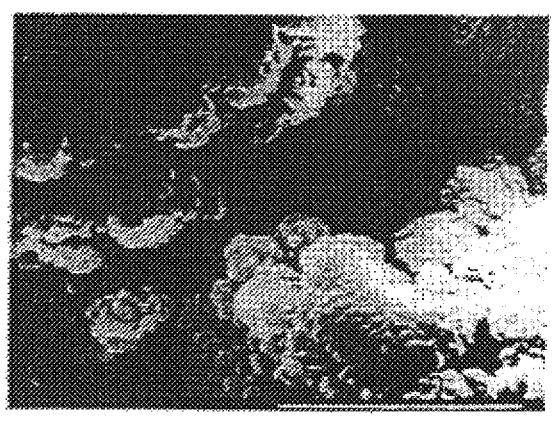
(b)

METHOD OF COMPRESSION MOULDING OF POLYMER POWDER AND PRODUCT PRODUCED

The present invention relates to compression moulding of high molecular weight polymers, and components made by these moulding processes.

The processing of ultra-high molecular weight polymers into load-bearing components by techniques conventional for thermoplastics is not feasible because of the exceptionally high viscosity of such materials. The polymer manufacturer produces a polymerised powder which then has to be compacted into a continuous solid. One method of compaction is to produce large slabs or rods by melting the powder and compressing or extruding the melt followed by cooling to form the solid. Individual components are then manufactured from this bulk stock by machining.

An alternative is direct net-shape compression moulding of the powder in heated moulds of an appropriate shape. A weighed charge of the powder is poured into the fixed part of the mould and pressure applied through the moving part of the mould. Components of the same dimensions in plan, but of different thickness, can be made by varying the weight of the charge.

In order to ensure the mechanical integrity of components and to maximise their strength and wear resistance, it is essential for the powder to be fully compacted. In addition, for there to be no residual planes of weakness at the original particle boundaries (which give rise to preferential sites for fatigue crack growth), the moulding process must achieve complete homogenisation of the polymer. The process of homogenisation of the polymer may also be described by the terms welding, diffusion, self-diffusion, consolidation, and/or fusion. Complete homogenisation requires two steps to be completed, aided by elevated pressure and temperature. Firstly, there must be complete compaction of the powder, with the particles being deformed and pressed into intimate contact (fully wetted) at the molecular level, with all voids removed. Secondly, the polymer chains must interdiffuse across the particle interfaces, until the entanglements on either side of the interfaces are fully knitted together, and no memory of the original boundaries remains.

For these two processes to be achieved, sufficient time is required for thermal conduction from the heated surfaces of the mould to raise the temperature in the centre of the mould to that required for homogenisation; in addition, this temperature must be maintained for a sufficiently long period of time for homogenisation to take place. Manufacturers do not reveal what pressure, time and temperature cycles are used in the production of their components and these doubtless vary from manufacturer to manufacturer.

Compression moulding techniques find particular application in the manufacture of joint replacement prostheses, such as artificial hip and knee joints.

Over 1 million joint replacements are implanted annually world-wide. Virtually all of them include ultra-high molecular weight polyethylene (UHMWPE) elements which provide a low-friction arthroplasty when articulating with polished metal surfaces.

Direct moulding has certain advantages, when compared to moulding of large slabs or rods, followed by machining. The only external machining marks are those of the mould and it is possible to achieve a highly smooth and glossy surface finish. Moreover, the polymer may be moulded around metallic inserts to produce composite components.

UHMWPE has been the most widely used material for bearing surfaces in total knee and hip joint replacement prostheses since the 1970s, because of its suitable properties of biocompatibility, high impact strength, low friction and high wear resistance (Li, S. and Burstein, A. H., *The Journal of Bone and Joint Surgery, Incorporated*, 76-A, 1080 (1994)). However, recent research into the microstructure of the material has shown that incomplete consolidation of the UHMWPE powder, resulting in "fusion defects", is implicated in the failure of the material due to fatigue (Mayor, M. D., Wrona, M., Collier, J. P. and Jensen, R. E., *Clinical Orthopaedics and Related Research*, 299, 92 (1994)). Cracking and delamination, specifically associated with fatigue failure, have been found in retrieved knee components. A large literature has been produced characterising the morphology of the wear particles, describing the cellular reactions to the particles, defining the effects of oxidisation and irradiation on the mechanical properties of the polymer, describing the results of wear tests in hip and knee simulators in the laboratory and retrieval studies of components removed from patients at revision. To minimise the occurrence of wear, cracking and deformation, there is an urgent need to improve understanding of the factors governing homogenisation and removal of fusion defects, and to develop reliable means of ensuring their absence, by proper engineering of the manufacturing process. In practice, there is a range of prosthesis designs in use, and each design of component is produced in a variety of sizes, to suit the needs of different patients. It is necessary to develop ideal moulding conditions for each size of component.

Therefore, there is a need for a flexible computer-aided engineering methodology, that can be used at the design stage for products to optimise the moulding process for each individual component. There has been virtually no discussion in the scientific community about optimising the moulding/manufacturing process, other than the demonstration that components produced by different manufacturers exhibit differing wear rates and have different molecular weights.

In the compression moulding of powders of high molecular weight such as UHMWPE, once the powder particle surfaces are in intimate contact, homogenisation requires interdiffusion of the polymer chains across the interfaces. This occurs by the motion of entangled polymer chains along tortuous paths defined by neighbouring molecules: a process known as reptation. When molecules of given molecular weight have reptated to the extent that their new shapes have no correlation with their original shapes, they are said to have reptated. The time taken for polymer chains to reptate increases strongly with molecular weight and a typical sample of UHMWPE is normally believed to contain a wide spectrum of molecular weights. Thus, to maximise homogenisation, it is necessary to mould articles where as much as possible of the polymer has reptated, and hence the maximum reptated molecular weight is as high as possible.

The practical problem for UHMWPE and the moulding of prostheses from UHMWPE is that homogenisation, wetting and molecular diffusion take place exceptionally slowly in UHMWPE even in the molten state. Moreover, they are highly sensitive to temperature time history, and therefore in a typical moulding will occur to differing extents in different parts of a moulding. The problem is exacerbated by the need for supplying moulded components in different sizes, according to the needs of the patient.

The present invention provides a method by which the bonding of already compacted particles of a polymer throughout a moulding of arbitrary size and shape can be controlled. A finite-element model of the component is formed, the continuous solid being represented as a mesh of tetrahedral, brick-shape or other elements, joined together at their apices. The temperature at the surface of the model component is taken through a cycle of elevated temperature followed by fall in temperature. Conventional theory of heat conduction is used to calculate numerically the time/temperature history throughout the component. Standard finite-element packages can be used for these calculations.

The maximum reptated molecular weight may be calculated as a function of position and time within the moulding, according to the equations below. The controlled cycle of time/temperature at the surface and/or the component design is modified until the calculation of reptated molecular weight shows that a satisfactory maximum reptated molecular weight is achieved throughout the moulding.

According to the present invention there is provided a process of compression moulding an article from a polymer powder comprising:

a) applying a polymer powder to a mould;
b) compacting the polymer powder by the application of a pressure P;
c) raising the temperature of the surface of the mould to a value above the melting temperature of the polymer powder; and
d) maintaining a temperature $T_M$ at the surface of the mould for a period of time $t_M$ and then cooling to a temperature below the crystallisation temperature of the polymer;

where $T_M$ and $t_M$ are controlled so as to provide a moulded article comprising a polymer of predetermined maximum reptated molecular weight ($\hat{M}$).

Preferably, $T_M$ is controlled so as to produce a moulded article comprising a polymer where the final, maximum reptated molecular weight $\hat{M}_f(x)$ of the polymer exceeds a specified value at all locations in the article. Preferably, $\hat{M}_f(x)$ for any given position x within the moulded article, is determined according to the following formula:

$$\hat{M}_f(x) = \left( \frac{D^* M^{*n} \xi(x, t_f)}{\beta} \right)^{\frac{1}{(1+n)}}$$

as discussed below where $t_f$ is the time at which the last point of the moulding is predicted to fall below a specified crystallisation temperature, $D^*$ is the self-diffusion coefficient for a reference polymer of molecular weight $M^*$, $\beta$ is a constant and n is defined by the relationship $$n = -\frac{\partial \ln D}{\partial \ln M}$$

where D is the self-diffusion coefficient of a monodisperse polymer of molecular weight M, and $\xi$ is an equivalent time at the reference temperature $T^*$ applying to $D^*$ calculated from the temperature-time history $T(x,u)$ $$\xi(x, t) = \int_0^t \frac{du}{a_T(x, u)}$$

where $a_T^{-1} = 0$ until the calculated temperature rises above a specified melting temperature, and then $$a_T^{-1} = \exp\left( \frac{Q}{R} \left[ \frac{1}{T^*} - \frac{1}{T} \right] \right)$$

until the calculated temperature falls below a specified crystallisation temperature; thereafter $a_T^{-1} = 0$.

$\hat{M}(x, t_M)$ is thus the maximum restated molecular weight calculated as a function of the position of and the time of the polymer in the mould.

As specified above, n is related to the self-diffusion coefficient D of a monodisperse polymer of molecular weight M by the equation:

$$n = -\frac{\partial \ln D}{\partial \ln M}$$

and n is to be determined from the appropriate experimental data. The best current determinations for the value of n is that it is in the range of from 2 to 2.5, in particular about 2.4.

Preferably, the polymer is polyethylene such as UHMWPE, and $T_M$ and $t_M$ are chosen to give $\hat{M}_f(x)$ in the range of from $3 \times 10^6$ g/mol to $6 \times 10^6$ g/mol. Other polymers may also be compression moulded according to the invention, for example ultrahigh molecular weight polypropylene or polytetrafluoroethylene.

Preferably, the pressure P is in the range 9 MPa to about 30 MPa.

Preferably, the process includes a cooling step, wherein the mould is cooled. The rate may be in the range of from 5–10 degrees Kelvin/min.

Also according to the invention there is provided a moulded article formed from a process of compression moulding a polymer powder comprising:

a) applying a polymer powder to a mould;
b) compacting the polymer powder by the application of a pressure P;
c) raising the temperature of the surface of the mould to a value above the melting temperature of the polymer powder; and
d) maintaining a temperature $T_M$ at the surface of the mould for a period of time $t_M$ and then cooling to a temperature below the crystallisation temperature of the polymer;

where $T_M$ and $t_M$ are controlled so as to provide a moulded article comprising a polymer of predetermined molecular weight ($\hat{M}_f(x)$) greater than a specified value.

According to a further aspect of the invention, the moulded polymer article is an orthopaedic prosthesis. The article may be a component of a joint replacement for the treatment of arthritis and other degenerative diseases of the joints, particularly of the knee, hip, shoulder, elbow, wrist, ankle, finger and toe joints.

Preferably, $T_M$ is controlled to give a moulded article comprising the polymer where the final, maximum reptated molecular weight $\hat{M}(x, t_M)$ exceeds a specified value at all locations in the article. Preferably, $\hat{M}_f(x)$ is determined according to the following formula:

$$\hat{M}_f(x) = \left( \frac{D^* M^{*n} \xi(x, t_f)}{\beta} \right)^{\frac{1}{(1+n)}}$$

as discussed below.

The temperature $T_M$ and the time $t_M$ for which this temperature is maintained at the mould surface, may be controlled to give a moulded article of a predetermined maximum reptated molecular weight.

Calculations are carried out to determine the specific time/temperature surface history required for every separate shape and size of component; these calculations result in a process that provides a moulded article of a polymer of maximum reptated molecular weight at least equal to a specified minimum value throughout the component.

As an example, calculations indicate that when the mould surface temperature is raised to 165° C. for 10 minutes, it can take uc to 45 minutes for the centre of a simple cylindrical moulding of UHMWPE, thickness 15 mm, to reach its maximum reptated molecular weight of $4.25 \times 10^6$ g/Mol, whereas the surface of the moulding does so in 30 minutes.

The present invention provides moulded articles of high strength and wear resistance. As examples, the articles may be UHMWPE articles for use as orthopaedic prostheses. High strength and wear resistance are particularly important in this application, as failure of the UHMWPE element of a prosthesis through cracking, or excess cold flow, can lead to an immediate need for a revision operation. Steady wearing away of the UHMWPE element is more insidious, but the small wear particles released can be consumed by the bone cells, leading to a hostile reaction, the formation of osteoclasts, the development of osteolysis and the loosening of the prosthesis.

The bulk of the orthopaedic components in current use are manufactured by machining from segments cut from compression moulded slabs or ram-extruded rods. Individually compression moulded components are increasingly being used. In either event, assurance of sufficient reptation time and a satisfactory maximum reptated molecular weight is needed to avoid the consequences of inadequate fusion of the polymer powder particles into a solid in which memory of the inter-particle interfaces is retained as sites of potential crack formation.

The present invention will be further described with reference to the accompanying drawings in which:

FIG. 1 shows scanning electron microscope (SEM) micrographs showing the as-polymerised UHMWPE powder morphology at two levels of magnification. The scale bars (a) and (b) represent 100 μm and 10 μm respectively;

Figure 5:
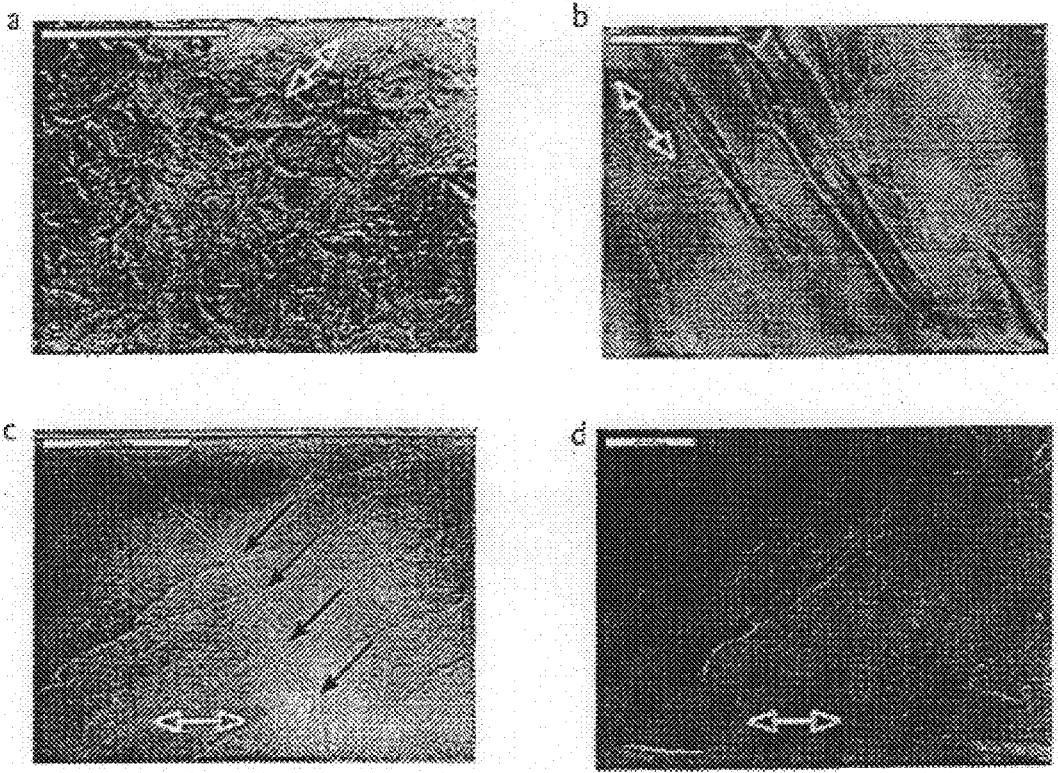
Figure 6:
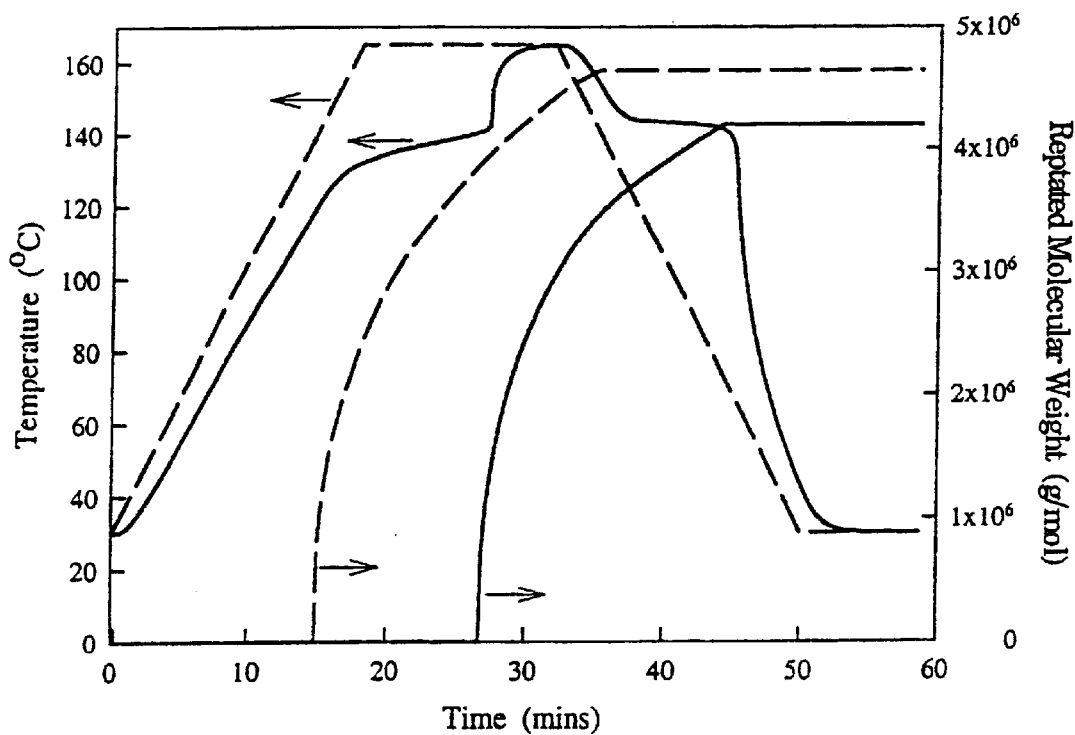
Figure 7:
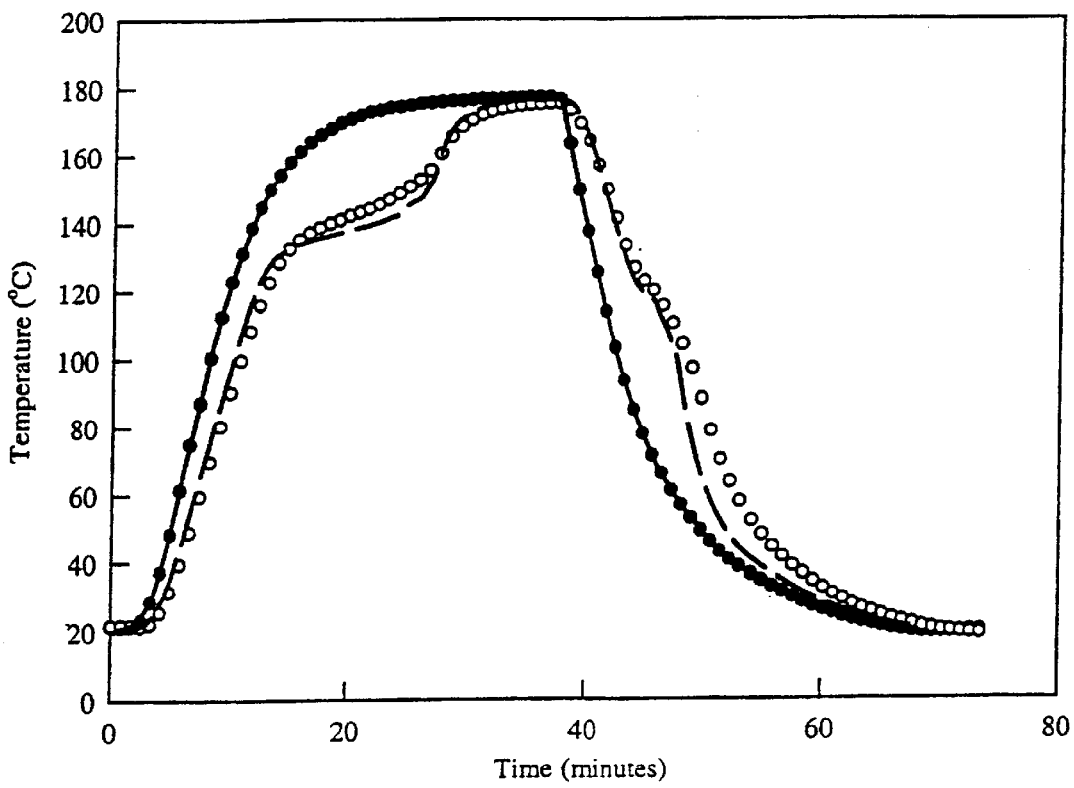

FIG. 5 shows SEM micrographs of side surfaces of UHMWPE machined tensile specimens after fracture, for various moulding conditions. The moulding temperature, dwell time and SEM scale bar are: (a) 145° C., 60 mins, 500 μm; (b) 165° C., 10 mins, 100 μm; (c) 165° C., 60mins, 200 μm; (d) 185° C., 10 mins, 200 μm. The white arrow indicates the direction of the tensile axis;

FIG. 6 shows results from the UHMWPE process model for cylindrical mouldings; mid-plane temperature and maximum reptated molecular weight $\hat{M}$ versus time, at external surface (dashed line) and centre line (solid line); and FIG. 7 provides a comparison of in-situ measured polymer data (symbols) with the thermal model simulations (lines). Filled and open symbols show measured temperature in the mould wail near to the polymer surface, and in the polymer near to the centre of the moulding, respectively. Full and dashed lines show model simulations at the polymer outer surface and near to the centre corresponding to the measured position, respectively.

The polymer material used in obtaining the results described with reference to the accompanying Figures was Hifax 1900H medical grade UHMWPE powder, which is as-polymerised and without any calcium stearate coating. The molecular weight of this material is notoriously difficult to determine, but is quoted by the manufacturers to be close to $5.3 \times 10^6$ g/mol, as determined from the intrinsic viscosity (method ASTM D4020-96).

The as-received powder was examined by scanning electron microscopy (SEM): particles were mounted directly onto an SEM stub and coated with a thin layer of gold-palladium alloy. FIG. 1 shows the typical particle morphology at two levels of magnification, and is similar to that reported previously for this material, for example by (Gao, P., Cheung, Man Ken, and Leung, T. Y., *Polymer*, 37 3265 (1996)), and for other grades of as-polymerised UHMWPE, see Farrar, D. F., and Brain, A. A., *Biomaterials*, 18, 1677 (1997). The particles size is typically 150 μm. They are clearly highly irregular, with many re-entrant surfaces. Moreover, they appear to be aggregates of even smaller particles, of typical dimension≈1 μm, presumably arising from different catalyst particles and fused together during polymerisation.

Thermal properties of the powder were evaluated by Differential Scanning Calorimetry (DSC), using a Perkin Elmer DSC-7 calorimeter, with sample masses of 3.6–3.7 mg and a scanning rate of 5K/min. The specific melting temperature of the powder referred to hereinbefore was determined as the temperature of peak flux during heating. Heats of fusion were obtained by calculating the area under the endothermic melting peak in the specific heat. The mass fraction degree of crystallinity was then determined by comparing the heat of fusion with that for a fully crystalline polyethylene (292.8 kJ/kg). For the as-received powder, the peak melting temperature, was found to be 141.7° C., and the crystallinity to be high: 76%. However, when the powder was heated beyond its melting point and then cooled at the same speed, the final crystallinity was much less: 44%. The specified crystallisation temperature of the polymer referred to hereinbefore was determined as the temperature of peak heat flux during cooling.

Cylindrical samples of UHMWPE (diameter=30 mm, length=15 mm) were compression-moulded from as-polymerised powder, using an instrumented mould allowing simultaneous measurement of temperature in the mould wall and (if necessary) in the polymer, and of pressure in the polymer at the mould wall. The moulding sequence was: (1) compaction by pressure in the solid state; (2) raising of the mould temperature to a value above the melting temperature of the polymer; (3) a constant-temperature dwell of 10 minutes or 60 minutes; (4) cooling of the mould at 7 K/min. Values of the maximum pressure were in the range 9 to 30 MPa. Temperature and pressure data were logged with a PC through a Biodata Microlink modular interface. The integrity of the resulting mouldings was then examined by means of mechanical tests and SEM.

In order to investigate the temperature-time effect on mechanical properties, the moulded specimens were studied using an Instron 4204 testing machine with environmental chamber. Miniature dumbell tensile specimens were machined from the compression mouldings and subjected to constant nominal strain-rate ($10^{-3}$ s$^{-1}$) tension tests at 37° C.

Figure 2:
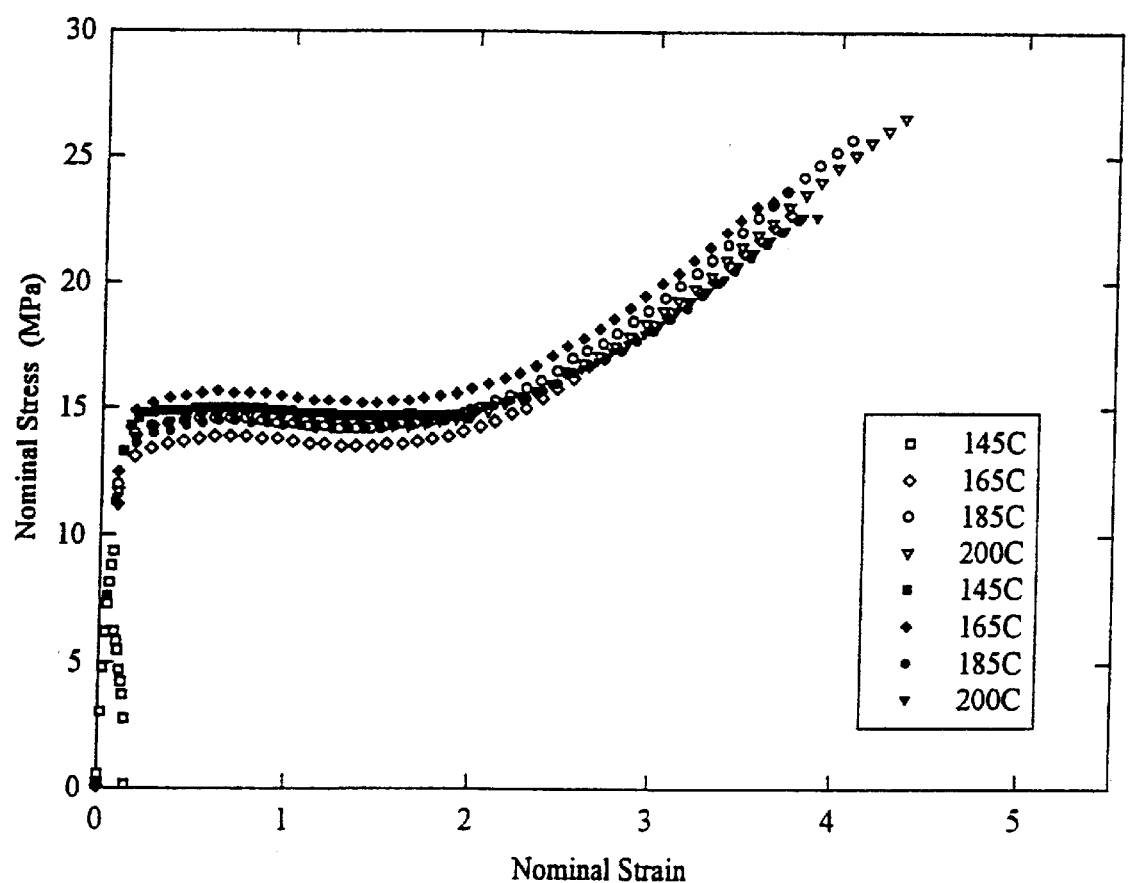
FIG. 2 shows the effect of processing variables on constant extension-rate ($10^{-3}$ s$^{-1}$) stress/strain curves at 37° C. of specimens cut from the surfaces of the mouldings. Moulding temperatures (° C.) as shown; open symbols indicate a dwell time of 10 mins; closed symbols a dwell of 60 mins.
Figure 3:
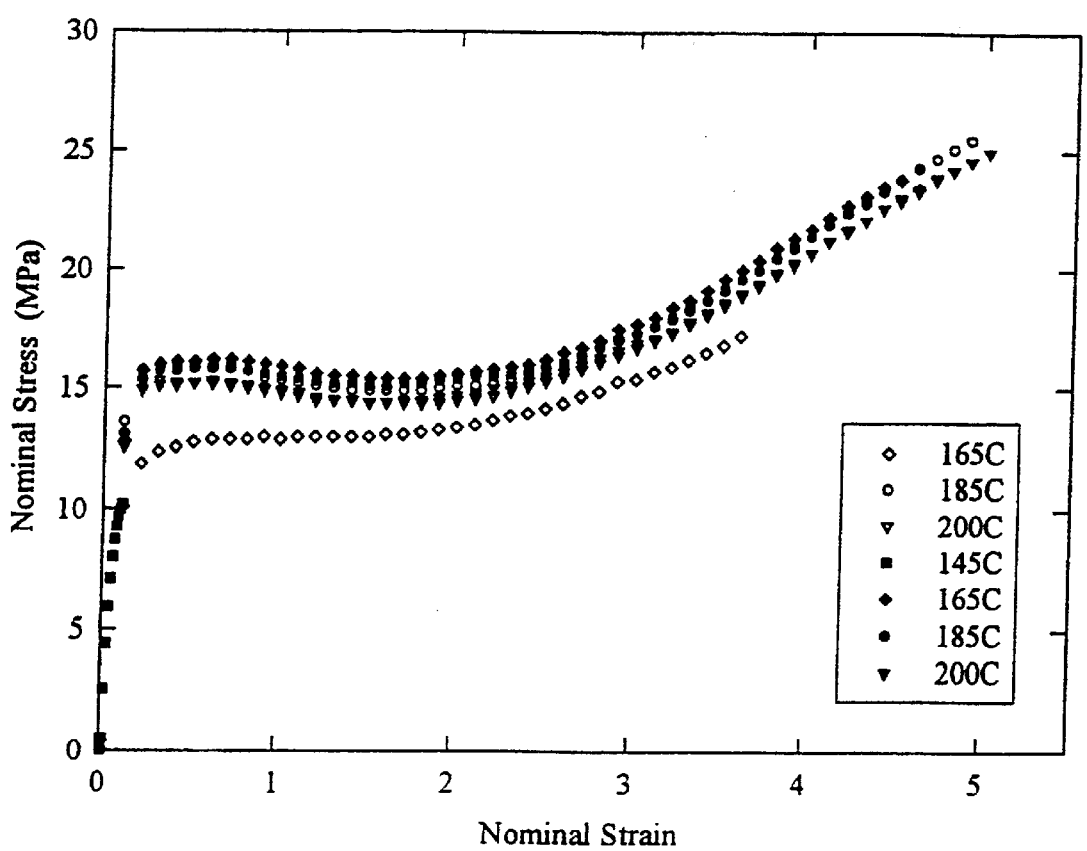
FIG. 3 shows the effect of processing variables on constant extension-rate ($10^{-3}$ s$^{-1}$) stress/strain curves at 37° C. of specimens cut from the centres of mouldings. Moulding temperatures (° C.) as shown: open symbols indicate a dwell time of 10 mins; closed symbols a dwell of 60 mins.

Mouldings prepared with different maximum temperatures and dwell times all gave stress-strain curves of similar shape see FIGS. 2 and 3 for results from specimens cut from the surfaces and centres of mouldings respectively.

They were all characterised by the usual yield and pseudo-plastic flow shown by this material, and there was little variation in stress levels between the curves. However, there were dramatic reductions in elongation to break and ultimate tensile stress at the lowest moulding temperature and time: evidence for weak inter-particle boundaries. In addition, for short moulding times (10 mins) this was more pronounced at the centres of mouldings than at the surface (compare FIGS. 2 and 3). The centres of mouldings prepared at 145° C. with a dwell of 10 mins were too brittle to machine into tensile specimens.

Figure 4:
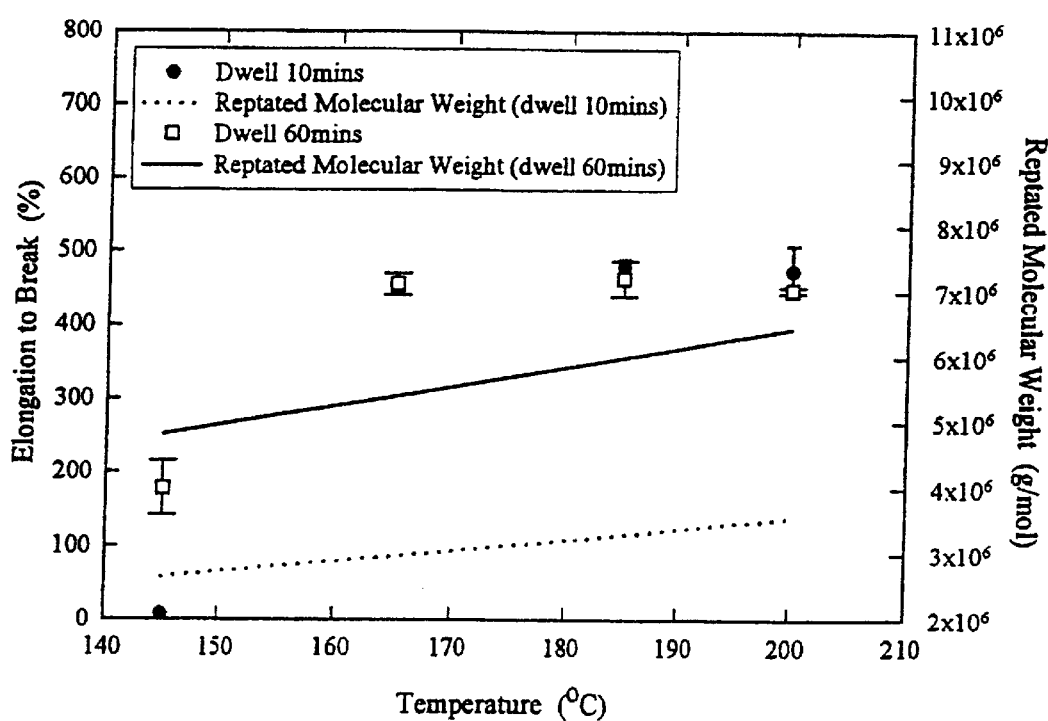
FIG. 4 shows variation of the measured elongation to break with moulding temperature, for two values of the dwell time $t_M$: specimens cut from the surfaces of mouldings (data points). Also shown (lines) are the corresponding values of calculated maximum reptated molecular weight $\hat{M}$.

This pattern of behaviour can also be seen in FIG. 4, where the measurements of elongation to break (mean of two specimens) are plotted versus mould temperature for two dwell times, for specimens cut from the surfaces of mouldings.

The broken tensile specimens were cut along the drawing direction with a microtome, and then mounted directly onto SEM stubs without gold coating, for examination of the free surfaces—as machined and stretched to failure. A Jeol microscope (type JSM-6300) was employed, operating at low voltage (1 kV) to minimise charging. Representative micrographs are shown in FIG. 5.

For a moulding temperature of 145° C. and a dwell of 60 minutes, SEM micrographs revealed poor consolidation (FIG. 5a). Clearly at this temperature there is significant voiding and weak interfaces between particles, and these have been opened up by the tensile testing; in spite of the voiding these specimens extended 200% before failure (FIG. 4). At 165° C. and a short moulding time (FIG. 5b), the most prominent features were a few elongated voids, resulting from a small residual void content in the mouldings, highly elongated during the extension by more than 450% to failure.

With a moulding temperature of 165° C. and the longer dwell time, and for higher temperatures, a different situation was found. There was negligible evidence for voiding: particles were well consolidated. Prior to extension, the surfaces of such specimens were featureless at this level of magnification. Nevertheless, new features were found after extension to break: linear surface markings on a length scale indicating the original particle boundaries, drawn out by the extension of ca 450% (see for example FIGS. 5c and d). Where a surface scratch happened to cross such a line, highly localised shear deformation was observed, see the points arrowed in FIG. 5. This indicates a plastic slip process occurring preferentially at the original particle boundaries, and reveals a memory of the inter-particle interfaces persisting even after extensive heating in the molten state. The explanation is to be found in the extended reptation time of a large proportion of the molecules present in UHMWPE.

This application describes a method which can be used to optimise the conditions of time and temperature for the moulding of components of various shape and sizes, using computer aided engineering of the moulding process to ensure that interpracticle boundaries are eradicated. The method exploits reptation theory, which governs the molecular self-diffusion by which molecular connectivity between original particles is achieved.

The long time taken for erasure of the original particle boundaries in FIG. 5 can be explained in terms of the slow self-diffusion of the long molecules in samples of UHMWPE. In conventional polyethylene melts, the rate-limiting step in the fusion of powder or granule particles above the melting temperature is the time required for heat transfer. Once in contact and molten, particles fuse by molecular diffusion across the interface in times of a few seconds.

Whereas, however, the thermal diffusivity has negligible dependence on molecular weight M, the self-diffusion coefficient D varies as $1/M^n$, where n is as hereinbefore defined. Thus, at sufficiently high molecular weights, such as in the regime of UHMWPE, the rate of self-diffusion becomes the rate-limiting step in achieving particle fusion. The need to avoid fusion defects in UHMWPE bearing surfaces in knee prostheses, especially, make it an urgent matter to achieve a quantitative understanding of this process, and to develop a predictive capability for use in product and process design. The theory of polymer diffusion by reptation provides a basis for such a model.

From FIG. 7 it can be seen that the in-situ measured temperature data correlates well with the simulation results before melting, in the melt stage and at crystallisation. For the melting transition phase the measured polymer temperatures are higher than the simulations.

It is known that when two polymer surfaces are brought into intimate contact, the time taken for the interface to become indistinguishable from the bulk, in terms of its mechanical properties, appears to be the reptatation time $t_r$ (Wool, R. P., Yuan, B.-L., an d McGarel, O. J., *Polym. Eng. and Sci.*,29, 1340 (1989)). This is to be expected, since $t_r$, is, by definition, the time taken for loss of correlation between the new molecular conformations and the original (Doi, M and Edwards, S. F., *The Theory of Polymer Dynamics*, Oxford University Press, Oxford (1986)). Only when this applies to those molecules adjacent to the interface will its identity have been erased.

Homogeneous, Isothermal Case

For a polymer of molecular weight M, the reptation time may be calculated from M and the self-diffusion coefficient D $$t_r = \beta \frac{M}{D} \quad (1)$$

where β is a constant specific to the chemistry of the particular polymer. Furthermore, another result from reptation theory is the molecular weight dependence of D, which combined with its temperature-dependence gives $$D \propto M^{-n} \exp\left(-\frac{Q}{RT}\right) \quad (2)$$

where Q is the activation energy for self-diffusion and R the universal gas constant.

Hence, if D is known at some reference molecular weight M* and temperature T*, then its value for a molecular weight M and temperature T can be obtained from $$D = D^*\left(\frac{M^*}{M}\right)^n \exp\left[\frac{Q}{R}\left(\frac{1}{T^*} - \frac{1}{T}\right)\right] \quad (3)$$

and the corresponding reptation time at temperature T is $$t_r = \frac{\beta}{D^* M^{*n}} M^{n+1} \exp\left[\frac{Q}{R}\left(\frac{1}{T} - \frac{1}{T^*}\right)\right] \quad (4)$$

An alternative interpretation is that, in a time t at temperature T, only molecules up to a molecular weight $\hat{M}$ are expected to have reptated, where $$\hat{M} = \left(\frac{D^*M^{*n}}{\beta}\right)^{1/(n+1)} t^{1/(n+1)} \exp\left[\frac{-Q}{(n+1)R}\left(\frac{1}{T} - \frac{1}{T^*}\right)\right] \quad (5)$$

In the case of polyethylene, the values of the parameters entering in β are well known, and the self-diffusion measurements made by Klein. J., *Nature*, 271, 143 (1978) provide the other required constants. Thus the maximum reptated molecular weight $\hat{M}$ may be calculated for a sample of polyethylene held in the melt state for a time t and temperature T, and this is included in FIG. 4 for the surfaces of the moulded samples. It is interesting to note that only at the longer time and highest mould temperatures does $\hat{M}$ approach a value of $5.3 \times 10^6$ g/mol, stated hereinbefore to apply to the molecular weight of the present UHMWPE. Clearly, in this material the degree of interface erasure will be highly sensitive to the precise temperature-time sequence seen by the polymer in the melt wring moulding, even assuming all particle surfaces are in intimate contact.

Inhomogenous, non-Isothermal Case

It follows from the above, that there is an urgent need to be able to interpret and predict spatial variations in inter-particle bonding within moulded components, and for this purpose the above treatment must be extended to inhomogenous, non-isothermal temperature histories. We therefore introduce the concept of a "reptation-equivalent" time ξ, which would produce the same degree of reptation—i.e. the same $\hat{M}$—isothermally at temperature T*, as the actual time t does following the actual thermal history. This can be done by introducing a time-temperature shift factor $a_T$ for self-diffusion, where $\xi = t a_T^{-1}$. $a_T^{-1} = 0$ until the temperature rises above a specified melting temperature of the polymer; and then $$a_T^{-1} = \exp\left(\frac{Q}{R}\left[\frac{1}{T^*} - \frac{1}{T}\right]\right) \text{ and } \xi = \frac{t}{a_T} \quad (6)$$

until the temperature falls below a specified crystallisation temperature. Thereafter, $a_T^{-1} = 0$. In the case of an inhomogeneous, non-isothermal temperature history T(x,u)

$$\xi(x,t) = \int_0^t \frac{du}{a_T(x,u)} \quad (7)$$

The maximum reptated molecular weight is then calculated as a function of position and time within the moulding $$\hat{M}(x,t) = \left(\frac{D^*M^{*n}\xi(x,t)}{\beta}\right)^{1/(n+1)} \quad (8)$$

This approach has been employed to compute the development of inter-particle reptation during moulding of three-dimensional components. Evolution of the temperature field was computed numerically with the ABAQUS Finite Element tool, and ξ(x,t) was carried through the calculation as a state variable. The assumption was made that reptation occurs only in the melt state: i.e. the rate of reptation (and hence $\alpha_T^{-1}$) is zero until melting and returns to zero on crystallisation. In this manner, the final value cf maximum reptated molecular weight $\hat{M}_f(x)$ was computed throughout the moulding. Sample results, for the cylindrical mouldings described above, are shown in FIG. 6. It is clear that, because of the finite time required for heat transfer by conduction, there is a substantial difference in the rates at which inter-particle reptation is expected to build up between the centre and surface of a moulding, and this is reflected in variations in $\hat{M}_f(x)$ and hence in the degree of interface erasure in the final product.

This fact, together with variations in degree of compaction also associated with temperature history variations, is responsible for the differences in mechanical response between specimens cut from the surfaces and centres of mouldings.

We have shown that the mechanical integrity of compression moulded UHMWPE is sensitive to the temperature-time history in the melt state during moulding. even for melt temperatures as high as 165° C. and 185° C. in this polymer, and after full compaction, there remains structural weakness at the boundaries of the original powder particles. This was revealed by SEM of the free surfaces of mouldings after extensive deformation at the in-use temperature for prostheses. At even lower melt temperatures, at the pressures employed in this work, residual voids due to imperfect compaction accentuate the inter-particle weakness and produce large reductions in elongation to break.

In practical compression moulding of UHMWPE, therefore, a high degree of powder compaction and void removal can be readily assured at higher moulding temperatures and times. The degree of interface erasure by inter-particle diffusion, however, will vary in practice throughout moulded components, and will be sensitive to details of the moulding sequence and of component shape. In this situation, it is useful to have a means of quantifying the progress of interface diffusion, and the non-isothermal model described above makes this possible.

What is claimed is:

1. A process of compression moulding an article from a polymer powder comprising:

a) applying a polymer powder to a mould;
   b) compacting the polymer powder by the application of a pressure P;
   c) raising the temperature of the surface of the mould to a value above the melting temperature of the polymer powder; and
   d) maintaining a temperature $T_M$ at the surface of the mould for a period of time $t_M$ and then cooling to a temperature below the crystallisation temperature of the polymer;

where $T_M$ and $t_M$ are controlled so as to provide a moulded article comprising a polymer of predetermined maximum reptated molecular weight ($\hat{M}$).

2. A process as claimed in claim 1 wherein the temperature, $T_M$, is controlled so as to produce a moulded article comprising a polymer where the final, maximum reptated molecular weight $\hat{M}_f(x)$ of the polymer exceeds a predetermined value at all locations in the article.

3. A process as claimed in claim 1 where the reptated molecular weight $\hat{M}_f(x)$ for any given position x within the moulded article is predetermined according to the formula:

$$\hat{M}_f(x) = \left(\frac{D^*M^{*n}\xi(x,t_f)}{\beta}\right)^{\frac{1}{(1+n)}}$$

where D* is the self-diffusion coefficient for a reference polymer of molecular weight M*, β is a constant and n is defined by the relationship $$n = -\frac{\partial \ln D}{\partial \ln M}$$

where D is the self-diffusion coefficient of a monodisperse polymer of molecular weight M, and $\xi$ is an equivalent time at the reference temperature T* applying to D* calculated from the temperature-time history T (x,u)

$$\xi(x, t) = \int_0^t \frac{du}{a_T(x, u)}$$

where $a_T^{-1} = 0$ until the calculated temperature rises above a specified melting temperature, and then $$a_T^{-1} = \exp\left(\frac{Q}{R}\left[\frac{1}{T^*} - \frac{1}{T}\right]\right)$$

until the calculated temperature falls below a specified crystallisation temperature; thereafter $a_T^{-1} = 0$.

4. A process as claimed in claim 3 wherein the value of n is about 2.4.

5. A process as claimed in claim 1 wherein the polymer is ultra high molecular weight polyethylene.

6. A process as claimed in claim 5 wherein the $T_M$ and $t_M$ are chosen so as to give a final maximum reptated molecular weight, $\hat{M}_f(x)$, of from $3 \times 10^6$ g/Mol to $6 \times 10^6$ g/mol.

7. A process as claimed in claim 1 wherein the polymer is ultra high molecular weight polypropylene or polytetrafluoroethylene.

8. A process as claimed in claim 1 wherein the pressure P is in the range of from 9 Mpa to 30 Mpa.

9. A moulded polymer article which is formed by a process as claimed in claim 1.

10. A moulded polymer article as claimed in claim 9 which is an orthopaedic prosthesis.

11. A moulded polymer article as claimed in claim 10 which is a component of a knee, hip, shoulder, elbow, wrist, ankle, finger or toe joint replacement.

* * * * *